United States Patent
Siegel et al.

(10) Patent No.: US 7,662,780 B2
(45) Date of Patent: Feb. 16, 2010

(54) ADMINISTERING HYPOCRETIN TO OBESE INDIVIDUALS

(75) Inventors: Jerome Siegel, Northridge, CA (US); Lisa Noelle Boehmer Murillo, Nambe, NM (US)

(73) Assignee: The Regents of the University of California, Oakland, CA (US)

( * ) Notice: Subject to any disclaimer, the term of this patent is extended or adjusted under 35 U.S.C. 154(b) by 387 days.

(21) Appl. No.: 10/526,110

(22) PCT Filed: Aug. 27, 2003

(86) PCT No.: PCT/US03/27038
§ 371 (c)(1),
(2), (4) Date: Nov. 18, 2005

(87) PCT Pub. No.: WO2004/019881
PCT Pub. Date: Mar. 11, 2004

(65) Prior Publication Data
US 2006/0241029 A1  Oct. 26, 2006

(51) Int. Cl.
*A61K 38/17* (2006.01)
*A61K 38/18* (2006.01)

(52) U.S. Cl. .............................. 514/12; 514/2
(58) Field of Classification Search ........................ None
See application file for complete search history.

(56) References Cited

U.S. PATENT DOCUMENTS 7,112,566 B1 * 9/2006 Siegel et al. ................... 514/12

7,335,640 B2 * 2/2008 Siegel et al. ................... 514/12

FOREIGN PATENT DOCUMENTS

WO 98/05352 * 2/1998

OTHER PUBLICATIONS

Taheri et al., Clinical Science (2001) 101(2, Supplement 45):17p. and Table of Contents.*
Alberts et al. 1994. Molecular Biology of the Cell pp. 129-130.*
Stricker-Krongrad 2002 Regulatory Peptides 104:11-20.*
Haynes, Andrea C., et al., "Effects of single and chronic intracerebroventricular administration of the orexins on feeding in the rat," Peptides 20 (1999) 1099-1105.
Preti, Antonio, "Orexins (hypocretins): Their role in appetite and arousal," Current Opinion in Investigational Drugs 2002, 3(8), 1199-1206.
De Lecea L, Kilduff T, Peyron C, Gao XB, Foye PE, Danielson PE, Fukahara C, Battenberg Elf, Gautvik VT, Barlett FS, Frankel WN, Van Den Pol AN, Bloom F, Gautvik KM, Sutcliffe JG (1998) The hypocretins: Hypothalamus-specific peptides with neuroexcitatory activity. Proc. Natl. Acad. Sci. USA 95:322-327.

(Continued)

*Primary Examiner*—Daniel E. Kolker
(74) *Attorney, Agent, or Firm*—Townsend and Townsend and Crew LLP

(57) ABSTRACT

The invention provides compositions and methods for treatment and prophylaxis of weight disorders. Such methods entail administering to an individual a therapeutically or prophylactically effective dosage regime of a hypocretin or an agonist thereof, and monitoring the condition of the individual responsive to the administering.

18 Claims, 2 Drawing Sheets

OTHER PUBLICATIONS

Dube MG, Kalra SP, Kalra PS (1999) Food intake elicited by central administration of orexins/hypocretins: identification of hypothalamic sites of action. Brain Res 842:473-477.

Edwards CM, Abusnana S, Sunter D, Murphy KG, Ghatei MA, Bloom SR (1999) The effect of the orexins on food intake: comparison with neuropeptide Y, melanin-concentrating hormone and galanin. J. Endocrinol. 160:R7-12.

Hara J, Beuckmann CT, Nambu T, Willie JT, Chemelli RM, Sinton CM, Sugiyama F, Yagami K, Goto K, Yanagisawa M, Sakurai T (2001) Genetic ablation of orexin neurons in mice results in narcolepsy, hypophagia, and obesity. Neuron 30:345-354.

Ida T, Nakahara K, Katayama T, Murakami N, Nakazato M (1999) Effect of lateral cerebroventricular injection of the appetite-stimulating neuropeptide, orexin and neuropeptide Y, on the various behavioral activities of rats. Brain Res 821:526-529.

John J, Wu MF, Siegel JM (2000) Systemic administration of hypocretin-1 reduces cataplexy and normalizes sleep and waking durations in narcoleptic dogs. Sleep Res. Online 3:23-28 http://www.sro.org/2000/John/23/.

Kiyashchenko Li, Mileykovskiy BY, Lai YY, Siegel JM (2001) Increased and decreased muscle tone with orexin (hypocretin) microinjections in the locus coeruleus and pontine inhibitory area. J. Neurophysiol. 85:2008-2016.

Levitt DR, Teitelbaum P (1975) Somnolence, akinesia, and sensory activation of motivated behavior in the lateral hypothalamic syndrome. Proc. Natl. Acad. Sci. U.S.A. 72:2819-2823.

Lin L. Faraco J, Kadotani H, Rogers W, Lin X, Qui X, De Jong P, Nishino S, Mignot E (1999) The REM sleep disorder canine narcolepsy is caused by a mutation in the hypocretin (orexin) receptor gene. Cell 98:365-376.

Sakurai T, Amemiya A, Ishii M, Matsuzaki I, Chemelli RM, Tanaka H, Williams SC, Richardson JA, Kozlowski GP, Wilson S, Arch JR, Buckingham RE, Haynes AC, Carr SA, Annan RS, Mcnulty DE, Liu WS, Terrett JA, Elshourbagy NA, Bergsma DJ, Yanagisawa M (1998) Orexins and orexin receptors: a family of hypothalamic neuropeptides and G protein-coupled receptors that regulate feeding behavior. Cell 92:573-585.

Schuld A, Hebebrand J, Geller F, Pollmacher T (2000) Increased body-mass index in patients with narcolepsy. Lancet 355:1274-1275.

Siegel JM (1999) Narcolepsy: A key role for hypocretins (orexins). Cell 98:409-412.

Sweet DC, Levine AS, Billington CJ, Kotz CM (1999) Feeding response to central orexins. Brain Res 821:535-538.

Thannickal TC, Moore RY, Nienhuis R, Ramanathan L, Gulyani S, Aldrich M, Cornford M, Siegel JM (2000) Reduced number of hypocretin neurons in human narcolepsy. Neuron 27:469-474.

Tritos NA, Mastaitis JW, Kokkotou E, Maratos-Flier E (2001) Characterization of melanin concentrating hormone and preproorexin expression in the murine hypothalamus. Brain Res 895:160-166.

Willie JT, Chemelli RM, Sinton CM, Yanagisawa M (2001) To eat or to sleep? Orexin in the regulation of feeding and wakefulness. Annu. Rev. Neurosci. 24:429-458.

Yamamato Y, Ueta Y, Date Y, Nakazato M, Hara Y, Serino R, Nomura M, Shibuya I, Matsukura S, Yamashita H (1999) Down regulation of the prepro-orexin gene expression in genetically obese mice. Brain Res Mol Brain Res 65:14-22.

Yamanaka A, Sakurai T, Katsumoto T, Yanagisawa M, Goto K (1999) Chronic intracerebroventricular administration of orexin-a to rats increases food intake in daytime, but has no effect on body weight. Brain Res 849:248-252.

* cited by examiner

ADMINISTERING HYPOCRETIN TO OBESE INDIVIDUALS

TECHNICAL FIELD

This invention resides in the fields of neurology and medicine, and is related to methods for the treatment of weight disorders and compositions useful therein.

BACKGROUND OF THE INVENTION

Weight disorders such as obesity affect a widespread portion of society. Over 300,000 deaths are annually attributed to weight disorders and weight-related conditions. While the underlying causes of such disorders remain unclear, many different weight loss methods and drugs have been proposed. These approaches tend to fall into one of four categories. The first category involves controlling the energy intake of the individual. This is most typically achieved through modification of appetite. This category also includes surgical procedures such as gastric partitioning, jejunoileal bypass, vagotomy, and jaw wiring, as well as pharmaceuticals for inhibiting fat digestion. Also included are behavioral approaches such as low calorie food selection. The second category involves controlling an individual's energy expenditure, or thermogenesis. Typically this is accomplished through exercise, or by administration of thermogenic agents. The third category involves regulating certain hormonal and other metabolic factors that control the amount of energy substrates that become available to cells and tissues. The fourth category involves controlling fat reserves by regulating lipogenesis and lipolysis in adipose tissue.

In general, these methods of treating excess weight have meet with no significant long term success. A clear need therefore exists for improved method and compositions for treating or preventing excess weight.

Hypocretin is a neuropeptide originally associated with feeding. This neuropeptide is synthesized in neurons of the periformical, dorsomedial, lateral, and posterior hypothalamus (Kiyashchenko et al., J. Neurophysiol. 85(5):2008-2016 (2002), and commonly exists in one of two different forms: hypocretin-1 and hypocretin-2. The hypocretins are also referred to as orexins (orexin-1 or orexin-A; and orexin-2 or orexin-B).

Orexin has been implicated in the regulation of ingestive and other behaviors. For example, orexin has been reported to induce feeding in rats (Dube et al., Brain Res. 842(2):473477 (1999); Kotz et al., Regul. Pept. 104(1-3):27-32 (2002); Mullett et al., Neuroreport 11(1):103-108 (2000); and Sweet et al., Brain Res. 821(2):535-538 (1999)). In fact, the name orexin was given to the hypocretin peptide by a group that concluded that it stimulated appetite (Sakurai et al. Cell 92(4):573-585 (1998)). The term "orexigenic" is defined as promoting the appetite.

Orexin receptor antagonist has been reported to reduce orexin induced feeding in rats (Haynes et al., Regul. Pept. 104(1-3):153-159 (2002); and Haynes et al., Regul. Pept. 96(1-2):45-51 (2000)), prompting a recommendation that orexin receptor antagonists have potential as anti-obesity agents. Other studies report that mice deficient in hypocretin or hypocretin cells are prone to gaining weight. Thus, the role of hypocretin in nutrition is unclear.

SUMMARY OF THE INVENTION

In one aspect, the invention provides a method of preventing or treating excess body weight in an individual. Some methods entail administering an effective dosage regime of a hypocretin or an agonist thereof to the individual. In some such methods, the agonist is a natural human hypocretin-1 or hypocretin-2. In some such methods, the effective dosage regime is administered to a peripheral tissue of the individual, whereby the hypocretin or agonist thereof crosses the blood brain barrier of the individual. In some methods, the individual has excess body weight before the administering step and the administering reduces the excess body weight. In some methods, the individual has excess body weight before the administering step and the administering prevents the development of further excess body weight. In some methods, the method further entails monitoring a sign of the excess body weight responsive to the administering. In some methods, the sign of the excess body weight is a body mass index, waist circumference, waist to hip ratio, skin fold thickness, body density, body weight, or body fat percentage of the individual. In some methods, the administering is by cerebrospinal injection, intracerebroventricular injection, intraparenchymal injection, intravenous infusion, intraperitoneal injection, transdermal delivery, intramuscular delivery, subcutaneous delivery, inhalation, or oral delivery. In some such methods, the administration is to any one or a combination of the first, second, third, and fourth ventricles of the individual's brain. In some methods, the individual suffers from a weight disorder. In some such methods, the weight disorder is due to a deficiency of a hypocretin, a hypocretin agonist, or a hypocretin receptor in the individual. In some methods, the weight disorder is due to a deficiency in a hypocretin receptor transduction pathway in the individual. In some methods, the individual suffers from obesity. In some such methods, the obesity is determined based on a sign of excess body weight selected from the group consisting of body mass index, waist circumference, waist to hip ratio, skin fold thickness, body density, body weight, and body fat percentage. In some methods, the individual has a body mass index of 30 or higher before beginning the administering step. In some methods, the individual is overweight. In some methods, the administering causes an increase in the individual's caloric output relative to the individual's caloric intake. In some methods, the hypocretin or agonist thereof is administered with a pharmaceutically acceptable carrier as a pharmaceutical composition. In some methods, the individual is free of narcolepsy.

In another aspect, the invention provides a method of increasing a motor or muscular activity in an individual, wherein the method entails administering an effective dosage regime of a hypocretin or an agonist thereof to the individual. In some such methods, the administering results in the increased motor or muscular activity in the individual. In some methods, the method further entails monitoring the motor or muscular activity in the individual responsive to the administering. In some such methods, the motor or muscular activity is monitored by a wrist actigraph. In some methods, the administering is by cerebrospinal injection, intracerebroventricular injection, intraparenchymal injection, intravenous infusion, intraperitoneal injection, transdermal delivery, intramuscular delivery, subcutaneous delivery, inhalation, or oral delivery. In some such methods, the administration is to any one or a combination of the first, second, third, and fourth ventricles of the individual's brain. In some methods, the individual suffers from a motor or muscular activity disorder. In some such methods, the motor or muscular activity disorder is due to a deficiency of a hypocretin, a hypocretin agonist, or a hypocretin receptor in the individual. In some methods, the motor or muscular activity disorder is due to a deficiency in a hypocretin receptor transduction pathway in the individual. In some methods, the increased motor or muscular activity in the individual reduces or inhibits the development of a sign of excess body weight in the individual. In some methods, the individual suffers from a weight disorder.

In another aspect, the invention provides methods of increasing a metabolism in an individual, wherein the method entails administering an effective dosage regime of a hypocretin or an agonist thereof to the individual. In some methods, the administering results in the increased metabolism in the individual. In some such methods, the method further entails monitoring the metabolism in the individual responsive to the administering. In some methods, the administering is by cerebrospinal injection, intracerebroventricular injection, intraparenchymal injection, intravenous infusion, intraperitoneal injection, transdermal delivery, intramuscular delivery, subcutaneous delivery, inhalation, or oral delivery. In some such methods, the administration is to any one or a combination of the first, second, third, and fourth ventricles of the individual's brain. In some methods, the individual suffers from a metabolism disorder. In some methods, the metabolism disorder is due to a deficiency of a hypocretin, a hypocretin agonist, or a hypocretin receptor in the individual. In some methods, the metabolism disorder is due to a deficiency in a hypocretin receptor transduction pathway in the individual. In some methods, the increased metabolism in the individual reduces or inhibits the development of a sign of excess body weight in the individual. In some methods, the individual suffers from a weight disorder.

In another aspect, the invention provides a pharmaceutical composition comprising a hypocretin or agonist thereof and a pharmaceutically acceptable carrier.

DETAILED DESCRIPTION

1. Definitions

Figure 1A:
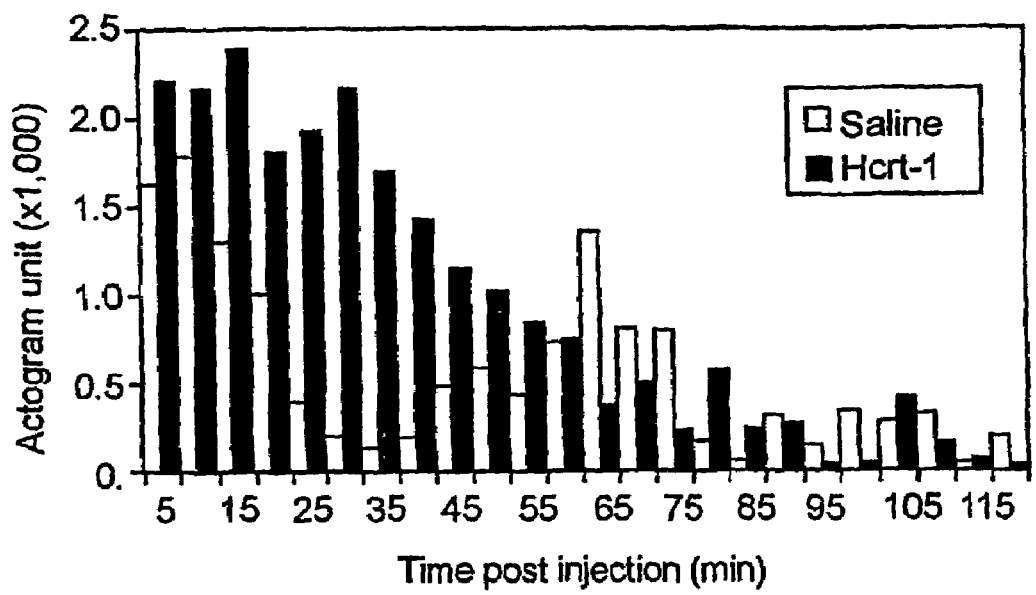
FIG. 1. Acute changes in motor activity after Hcrt-1 administration. (a) A representative actigraph record (5 minute bins) showing the activity level during the 2 hr period following Hcrt-1 (3 μg/kg) and normal saline. Hcrt-1 produced an increase in motor activity within 5 minutes of injection that persisted for 60 minutes. (b) The increase of motor activity was statistically significant at 0-30 and 30-60 minutes after orexin administration, as compared to saline control. In (b) values are mean±SE, *$p<0.05$; **$p<0.01$, Newman-Keuls test.

The term individual includes mammals, such as humans, domestic animals such as dogs or cats, farm animals such as cattle, horses, or pigs, monkeys, rabbits, rats, mice, and other laboratory animals.

The term molecule is used broadly to mean an organic or inorganic chemical such as a drug; a peptide, including a variant, analog, homolog, agonist, modified peptide or peptide-like substance such as a peptidomrnimetic or peptoid; or a protein such as an antibody or a fragment thereof, such as an $F_v$, $F_c$ or $F_{ab}$ fragment of an antibody, which contains a binding domain. A molecule can be nonnaturally occurring, produced as a result of in vitro methods, or can be naturally occurring, such as a protein or fragment thereof expressed from a cDNA library.

The terms polypeptide, peptide, and protein are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be expressed recombinantly and cleaved by enzymatic digest, expressed from a sequence encoding a peptide, or synthesized using standard techniques.

Stringent hybridization conditions are conditions under which a probe will hybridize to its target subsequence, typically in a complex mixture of nucleic acid, but not to other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

The term sequence identity means that two polynucleotide sequences are identical (i.e., on a nucleotide-by-nucleotide basis) over a window of comparison. The term "percentage of sequence identity" is calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

As applied to polypeptides, the term substantial identity means that two peptide sequences, when optimally aligned, such as by the programs GAP or BESTFIT using default gap weights (described in detail below), share at least about 80 percent sequence identity, preferably at least about 90 percent sequence identity, more preferably at least about 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected.

A preferred example of an algorithm that is suitable for determining percent sequence identity and sequence similarity is the FASTA algorithm, which is described in Pearson, W. R. & Lipman, D. J., 1988, Proc. Natl. Acad. Sci. U.S.A. 85:2444. See also W. R. Pearson, 1996, Methods Enzymol. 266:227-258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Another preferred example of algorithm that is suitable for determining percent sequence identity and sequence similarity are the BLAST and BLAST 2.0 algorithms, which are described in Altschul et al., 1977, Nuc. Acids Res. 25: 3389-3402 and Altschul et al., 1990, J. Mol. Biol. 215: 403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., spra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, Proc. Natl. Acad. Sci. U.S.A. 89: 10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Natl. Acad. Sci. U.S.A. 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, 1987, J. Mol. Evol. 35:351-360. The method used is similar to the method described by Higgins & Sharp, 1989, CABIOS 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984, Nuc. Acids Res. 12:387-395.

Another preferred example of an algorithm that is suitable for multiple DNA and amino acid sequence alignments is the CLUSTALW program (Thompson, J. D. et al., 1994, Nucl. Acids. Res. 22:4673-4680). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, 1992, Proc. Natl. Acad. Sci. U.S.A. 89:10915-10919).

The term specific binding (and equivalent phrases) refers to the ability of a binding moiety (e.g., a receptor, antibody, hypocretin or agonist thereof, ligand or antiligand) to bind preferentially to a particular target molecule (e.g., ligand or antigen) in the presence of a heterogeneous population of proteins and other biologics (i.e., without significant binding to other components present in a test sample). Typically, specific binding between two entities, such as a ligand and a receptor, means a binding affinity of at least about $10^6$ $M^{-1}$, and preferably at least about $10^7$, $10^8$, $10^9$, or $10^{10}$ $M^{-1}$. Specific (or selective) binding can be assayed (and specific binding molecules identified) according to the method of U.S. Pat. No. 5,622,699; this reference and all references cited therein are incorporated herein by reference. Typically a specific or selective reaction according to this assay is at least about twice background signal or noise and more typically at least about 5 or at least about 100 times background, or more.

The term label or labeled refer to incorporation of a detectable marker, e.g., a radiolabeled amino acid or a recoverable label (e.g., biotinyl moieties that can be recovered by avidin or streptavidin). Recoverable labels can include covalently linked polynucleotide sequences that can be recovered by hybridization to a complementary sequence polynucleotide or PNA; such recoverable sequences typically flank one or both sides of a nucleotide sequence that imparts the desired activity, i.e., binding to a hypocretin receptor. Various methods of labeling PNAs and polynucleotides are known in the art and can be used. Examples of labels include, but are not limited to, the following: radioisotopes (e.g., $^3H$, $^{14}C$, $^{35}S$, $^{125}I$, $^{131}I$, fluorescent or phosphorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for antibodies, transcriptional activator polypeptide, metal binding domains, epitope tags). Labels can also be attached by spacer arms of various lengths, e.g., to reduce potential steric hindrance.

The term excess body weight refers to that amount of an individual's weight that exceeds an ideal body weight or target body weight of the individual. The term ideal body weight (IBW) refers to a model body weight as determined by one of many commonly accepted standards. For example, ideal body weight can be calculated using the following formulas: IBW(kg) males=50+2.3[height (inches)−60]; and IBW(kg) female=45.5+2.3[height (inches)−60]. The term target body weight refers to a body weight that is selected by or for an individual with or without the advise of a medical or dietary advisor, and signifies a body weight which an individual seeks to attain or approach or a body weight which has otherwise been prescribed for the individual. A target body weight can be equal to an ideal body weight. Alternatively, a target body weight may be greater or less than an ideal body weight.

The term a sign of excess body weight refers to a body mass index, waist circumference, waist to hip ratio, body density, body weight, body fat, or body fat percentage of the individual.

The term body mass index (MI) refers a measure of body fat. The BMI of an individual is derived in a two-step mathematical formula. The individual's weight in pounds is first multiplied by 703. The product of the first step is then divided by the square of the individual's height in inches. In a metric version, BMI is calculated as the individual's weight in kilograms divided by the square of their height in meters. BMI is a frequently used medical standard to evaluate overweight and obesity.

The term waist circumference refers to a measure of abdominal fat content. The waist circumference of an individual is commonly determined using a tape measure placed comfortably around the smallest area below the rib cage and above the umbilicus (belly button). Alternatively, the waist circumference may be measured at the natural waist, between the palpated iliac crest and the palpated lowest rib margin at the mid axillary line.

The term waist-to-hip ration (WHR) refers to the ratio of an individual's waist circumference to hip circumference, and is mathematically calculated as the waist circumference divided by the hip circumference. The waist circumference can be measured as described above. The hip circumference is commonly determined using a tape measure placed comfortably around the largest extension of the buttocks.

The term body density refers to the individual's mass divided by the individual's volume, and is inversely proportional to the individual's body fat. In other words, the higher the body fat, the lower the body density.

The term body weight refers to an individual's weight. In a strict sense, body weight is equal to body mass multiplied by the acceleration of gravity. For the purposes of the present application, however, the terms body mass and body weight are interchangeable.

The term body fat percentage refers to the percentage of fat in an individual. Body fat percentage is the ratio of fat mass to total body mass, and an individual's total body mass is the sum of the fat mass (FM) and fat free mass (FFM). Fat mass can be defined as the total lipid mass of the body, while fat free mass, or lean mass, is the mass of bone, muscle, blood, and other nonfat tissue. As further discussed below, there are several methods available for determining body fat mass or percentage, such as skin fold thickness, hydrostatic weighing, ultrasound, near-infrared spectrophotometry, total body water, total body potassium, isotope dilution, photon absorptiometry, hydrostatic weighing, radiography, ultrasound, nuclear magnetic resonance, total body electrical conductivity, bioelectrical impedance analysis, infrared, computed tomography, and the like.

The term motor activity refers to the movement of an individual, including voluntary movement, which is purposeful, and involuntary movement, which is reflexive in nature. Often, motor activity is the result of coordinated muscular contractions.

The term muscular activity refers to muscular contractions that may or may not results in the movement of a body part. Muscular activity can be monitored by electromyography (EMG), which is the measurement of electrical activity that occurs within muscle fibers in response to nervous stimulation.

The term metabolism refers to the transformation by which energy is made available for the uses of the individual. Metabolism can be defined as the means by which the body derives energy and synthesizes the other molecules it needs from the fats, carbohydrates and proteins eaten as food, by enzymatic reactions helped by minerals and vitamins. Another definition of metabolism is the biochemical process of combining nutrients with oxygen to release the energy needed for the body to function. Metabolism can also be defined as the sum total of all anabolic (e.g., protein synthesis, muscle contraction, and active transport) and catabolic (e.g., cellular respiration) biochemical processes occurring in the cells of the individual's body.

The term metabolic rate refers to the rate at which an individual uses energy. This is also known as the rate of metabolism, or the rate of energy consumption, and reflects the overall activity of the individual's metabolism. Metabolic rate can be defined as the calories needed for maintaining body functions, daily activity (occupational and lifestyle), the thermic effect of food, and the energy cost of exercise. The term metabolic rate can also be defined as the rate of conversion of chemical energy into heat. Another definition of metabolic rate is the amount of energy that an individual's body is burning, or the rate at which calories are used The term metabolic rate can also refer to the rate at which anabolic and catabolic reactions of the individual's body operate.

The term basal metabolism refers to the minimum amount of energy required to maintain vital functions in an individual at complete rest, measured by the basal metabolic rate in a fasting individual who is awake and resting in a comfortably warm environment.

The term basal metabolic rate refers to the rate at which energy is used by an individual at complete rest. Basal metabolic rate is measured in humans by the heat given off per unit time, and expressed as the calories released per kilogram of body weight or per square meter of body surface per hour. Heart beat, breathing, maintaining body temperature, and other basic bodily functions all contribute to basal metabolic rate. Basal metabolic rate can also be defined as the stable rate of energy metabolism measured in individuals under conditions of minimum environmental and physiological stress, or essentially at rest with no temperature change. The basal metabolic rate among individuals can vary widely. One example of an average value for basal metabolic rate is about 1 calorie per hour per kilogram of body weight.

The term calorie refers to the amount of energy, e.g. heat, required to raise the temperature of 1 gram of water by 1° C. In medicine, nutrition, and the exercise sciences, the calorie is often used to describe what is actually the kilocalorie. A kilocalorie is the amount of energy needed to increase the temperature of 1 kilogram of water by 1° centigrade. One kilocalorie equals 1000 calories. The kilocalorie is abbreviated as kc, kcal or Cal, whereas the calorie or gram calorie is abbreviated as cal.

The term isocaloric balance refers to the condition in which an individual's caloric output is equal to their caloric intake. If an individual is in isocaloric balance, their body weight will remain stable. The term negative caloric balance refers to the condition in which an individual's caloric intake is less than their caloric output. If an individual is in negative caloric balance, their body weight will decrease. The term positive caloric balance refers to the condition in which an individual's caloric intake is greater than their caloric output. If an individual is in positive caloric balance, their body weight will increase.

2. General

The invention provides prophylactically and therapeutically effective dosage regimes for administering hypocretin to individuals having excess body weight. Although practice of the present methods is not dependent on an understanding of mechanism, it is believed that activation of the hypocretin receptor transduction pathway plays a role in reducing excess body weight in an individual by increasing muscle activity, metabolism, or both, without recruiting a commensurate increase in appetite.

The term hypocretin (Hcrt) refers to one of two hypocretin peptides: hypocretin-1 (Hcrt-1) and hypocretin-2 (Hcrt-2). These peptides are also commonly referred to as Orexin-A (OXA) and Orexin-B (OXB), respectively. The hypocretin neuropeptides are derived from prepro-hypocretin prepro-orexin), a precursor molecule. Some authors report that prepro-hypocretin and prepro-orexin are the same peptide, but that hypocretins are different from orexins. However, this is a minority view. (Smart et al., Br. J. Pharmacol. 129(7):1289-91 (2000)). Hypocretin-2 has been reported as a less stable form of hypocretin than hypocretin-1. More stable forms of hypocretin can be made, however, using known techniques. Human orexin-A is reported as a 33 residue peptide of 3562 Da, and human orexin-B is reported as a 28 residue peptide of 2937 Da, and the human prepro-orexin gene has been located at human chromosome 17q21 (Sakurai et al., Cell 92:573-585 (1998)). The whole length of the human prepro-orexin gene and corresponding cDNA has been cloned by Sakurai et al., J. Biol. Chem. 274(25):1771-1776 (1999). The human preproorexin gene consists of two exons and one intron distributed over 1432 base pairs, and is thought to encode a precursor peptide that is proteolytically processed into two orexin-A and orexin-B. Reference to hypocretin or orexin (or the precursor) includes the amino acid sequences discussed below, and allelic, cognate, and induced variants thereof. Usually such variants show at least 90% sequence identity to these exemplary sequences. Cognate forms of the human orexin sequence have been cloned from porcine tissues by Dyer et al., Domest. Anim. Endocrinol. 16(3):1450148 (1999). The term hypocretin also includes fragments of hypocretin peptide having the same or similar functional effect as hypocretin. As used in this application, the term hypocretin can also refer to an agonist thereof.

The term hypocretin receptor refers to one of two hypocretin receptor molecules: hypocretin receptor 1 (HCRTR1) and hypocretin receptor 2 (HCRTR2). These peptides are also commonly referred to as orexin receptor 1 (Ox1r) and orexin receptor 2 (Ox2r). The hypocretin receptors are G protein-coupled receptors, and activation of these receptor has been shown to result in an phospholipase C-mediated release of calcium from intracellular stores, with subsequent calcium influx (Smart et al., Br. J. Pharmacol. 128(1):1-3 (1999)). Reference to hypocretin receptor includes the amino acid sequences discussed below, and allelic, cognate, and induced variants thereof. Usually such variants show at least 90% sequence identity to these exemplary sequences. The term hypocretin receptor also includes fragments of hypocretin receptor peptide having the same functional effect as hypocretin receptor.

Several authors have reported sequence data for hypocretin precursor, hypocretin, and hypocretin receptors. Sakurai et al., Cell 92(4):573-585 (1998) report human orexin precursor, orexin receptors 1 and 2; rat orexin precursor; mouse orexin precursor; and bovine orexin-A. Hungs et al., Genome Res. 11(4):531-539 (2001) report canine orexin precursor. Dyer et al., Domest. Anim. Endocrinol. 16(3):1450148 (1999) report porcine orexin precursor. In a direct submission to GenBank, Szendro et al. report mouse orexin receptor 2 (Accession No. P58308). Peyron et al., Nat. Med. 6(9):991-997 report human hypocretin receptor 2. De Lecea et al., Proc. Natl. Acad. Sci U.S.A. 95(1):322-327 (1998) report human orexin receptors 1 and 2. Taketani et al., Genomics 29(3):698-703 (1995) report orexin precursor. Yeager et al., in an unpublished submission to GenBank, report hypocretin receptor 1 (Accession No. AY 070269).

The hypocretin polypeptide of the present invention can be modified to provide a variety of desired attributes, e.g., with improved pharmacological characteristics, while increasing or at least retaining substantially all of the biological activity of the unmodified peptide. For example, the hypocretin peptide or fragment thereof can be modified by extending or decreasing the amino acid sequence of the peptide. Substitutions with different amino acids or amino acid mimetic can also be made. As an example, truncated peptide analogues of orexin-A have been prepared and their biological activity assessed at the orexin-1 receptor (Darker et al., Bioorg. Med. Chem. Lett. 11(5):737-40 (2001)).

The hypocretin peptides employed in the subject invention need not be identical to natural proteins, so long as the subject peptides are able to induce a same or similar response against the desired hypocretin receptor molecule. Thus, a number of conservative substitutions (described in more detail below) can be made without substantially affecting the activity of hypocretin.

Single amino acid substitutions, deletions, or insertions can be used to determine which residues are relatively insensitive to modification. Substitutions are preferably made with small, relatively neutral moieties such as Ala, Gly, Pro, or similar residues. The effect of single amino acid substitutions can also be probed using D-amino acids. The number and types of residues which are substituted or added depend on the spacing necessary between essential contact points and certain functional attributes which are sought (e.g., hydrophobicity versus hydrophilicity). Increased activity can also be achieved by such substitutions, compared to the native Hcrt peptide. In any event, such substitutions should employ amino acid residues or other molecular fragments chosen to avoid, for example, steric and charge interference which might disrupt binding.

The substituting amino acids, however, need not be limited to those naturally occurring in proteins, such as L-$\alpha$-amino acids, or their D-isomers. The peptides can be substituted with a variety of moieties such as amino acid mimetics. The individual residues of the Hcrt polypeptides can be incorporated in the peptide by a peptide bond or peptide bond mimetic. A peptide bond mimetic of the invention includes peptide backbone modifications. Such modifications include modifications of the amide nitrogen, the $\alpha$-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983). Several peptide backbone modifications are known, these include, $\psi[CH_2S]$, $\psi[CH_2NH]$, $\psi[CSNH_2]$, $\psi[NHCO]$, $\psi[COCH_2]$ and $\psi[(E)$ or $(Z)$ CH=CH]. The nomenclature used above, follows that suggested by Spatola, above. In this context, $\psi$ indicates the absence of an amide bond. The structure that replaces the amide group is specified within the brackets.

Amino acid mimetics can also be incorporated in the peptides. An amino acid mimetic as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit a response against the appropriate hypocretin receptor molecule. Amino acid mimetics can include non-protein amino acids, such as $\beta$-$\gamma$-$\delta$-amino acids, $\beta$-$\gamma$-$\delta$-imino acids (such as piperidine-4-carboxylic acid) as well as many derivatives of L-$\alpha$-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) *Ann. Repts. Med. Chem.* 24:243-252.

As noted above, the peptides employed in the subject invention need not be identical, but can be substantially identical, to the sequence of the hypocretin molecule. The peptides can be subject to various changes, such as insertions, deletions, and substitutions, either conservative or non-conservative, where such changes might provide for certain advantages in their use. The polypeptides of the invention can be modified in a number of ways and still comprise a sequence substantially identical (as defined above) to a sequence in the naturally occurring Hcrt peptide molecule. The activity of the agonist can also be based on similar three dimensional or ionic characteristics which it shares with the native peptide or fragment thereof, without necessarily sharing substantial sequence identity with the native hypocretin or fragment thereof An agonist of a native polypeptide is a compound having a qualitative biological activity in common with the native polypeptide (described in detail below). For the purpose of the present invention, an agonist of a native hypocretin is defined by its ability to bind with and stimulate or activate a hypocretin receptor or increase the interaction of hypocretin with its receptor. For example, an agonist of hypocretin can bind to a native hypocretin receptor, triggering intracellular events that cause changes in membrane polarization, cause the release of other neurotransmitters, cause changes in the response to other neurotransmitters, or initiate other physiological or pharmacological responses characteristic of the receptor. Hypocretin agonists of the present invention preferably have at least about 60%, more preferably at least about 70%, even more preferably at least about 80%, most preferably at least about 90% overall amino acid sequence identity with a native sequence hypocretin polypeptide, preferably a human hypocretin as described by Sakurai T., et al., 1998, Cell 92:573-85 and de Lecea, L., et al., 1998, Proc. Natl. Acad. Sci. U.S.A. 95:322-327 (Genbank REFSEQ Accession Nos. NM 001524, NM 001525, and NM 001526). The hypocretin agonists show at least about 80%, more preferably at least about 90% and most preferably at least about 95% or more amino acid sequence identity with the binding domain of the hypocretin polypeptide sequence. Fragments of native sequence hypocretin polypeptides from various mammalian species and sequences homologous to such fragments constitute another preferred group of hypocretin agonists. Such fragments preferably show at least about 80%, more preferably at least about 90%, most preferably at least about 95% or more sequence identity with the hypocretin polypeptide sequence. Another preferred group of hypocretin agonists is encoded by nucleic acid hybridizing under stringent conditions to the complement of nucleic acid encoding a native hypocretin polypeptide. A further preferred group of hypocretin agonists include those compounds or molecules that enhance or otherwise facilitate the binding between a hypocretin receptor and its associated ligand, or that enhance or otherwise facilitate the stimulatory effect of the associated ligand on the hypocretin receptor or related polypeptide.

Agonists of the present invention can be expressed recombinantly and cleaved by enzymatic digest, expressed from a sequence encoding a peptide, synthesized using standard techniques, or derived from natural sources. Often, test compounds are screened for agonist activity. Compounds constituting agents, conjugates or conjugate moieties to be screened can be naturally occurring or synthetic molecules. Natural sources include sources such as, e.g., marine microorganisms, algae, plants, animals, and fungi. Alternatively, compounds to be screened can be from combinatorial libraries of agents, including peptides or small molecules, or from existing repertoires of chemical compounds synthesized in industry, e.g., by the chemical, pharmaceutical, environmental, agricultural, marine, cosmoceutical, drug, and biotechnological industries. Compounds can include, e.g., pharmaceuticals, therapeutics, environmental, agricultural, or industrial agents, pollutants, cosmoceuticals, drugs, organic compounds, lipids, glucocorticoids, antibiotics, peptides, sugars, carbohydrates, and chimeric molecules.

A variety of methods are available for producing peptide libraries (see, e.g., Lam et al., *Nature*, 354:82, 1991 and WO 92/00091; Geysen et al., *J Immunol Meth*, 102: 259, 1987: Houghten et al., *Nature*, 354: 84, 1991 and WO 92/09300 and Lebi et al., *Int J Pept Prot Res*, 41,201, 1993). Peptide libraries can also be generated by phage display methods. See, e.g., Dower, U.S. Pat. No. 5,723,286.

Combinatorial libraries can be produced for many types of compounds that can be synthesized in a step-by-step fashion (see e.g., Ellman & Bunin, *J Amer Chem Soc*, 114:10997, 1992 (benzodiazepine template), WO 95/32184 (oxazolone and aminidine template), WO 95/30642 (dihydrobenzopyran template) and WO 95/35278 (pyrrolidine template). Libraries of compounds are usually synthesized by solid phase chemistry on particle. However, solution-phase library synthesis can also be useful. Strategies for combinatorial synthesis are described by Dol+Le & Nelson, *J. Combinatorial Chemistry* 1. 235-282 (1999)) (incorporated by reference in its entirety for all purposes). Synthesis is typically performed in a cyclic fashion with a different monomer or other component being added in each round of synthesis. Some methods are performed by successively fractionating an initial pool. For example, a first round of synthesis is performed on all supports. The supports are then divided into two pools and separate synthesis reactions are performed on each pool. The two pools are then further divided, each into a further two pools and so forth. Other methods employ both splitting and repooling. For example, after an initial round of synthesis, a pool of compounds is split into two for separate syntheses in a second round. Thereafter, aliquots from the separate pools are recombined for a third round of synthesis. Split and pool methods result in a pool of mixed compounds. These methods are particularly amenable for tagging as described in more detail below. The size of libraries generated by such methods can vary from 2 different compounds to $10^4$, $10^6$, $10^8$, or $10^{10}$, or any range therebetween.

Preparation of encoded libraries is described in a variety of publications including Needels, et al., *Proc. Natl. Acad. Sci. USA* 1993, 90, 10700; Ni, et al., *J. Med. Chem.* 1996, 39, 1601, WO 95/12608, WO 93/06121, WO 94/08051, WO 95/35503 and WO 95/30642 (each of which is incorporated by reference in its entirety for all purposes). Methods for synthesizing encoded libraries typically involve a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. The monomer set can be expanded or contracted from step to step; or the monomer set could be changed completely for the next step (e.g., amino acids in one step, nucleosides in another step, carbohydrates in another step). A monomer unit for peptide synthesis, for example, can include single amino acids or larger peptide units, or both.

Compounds synthesizable by such methods include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Prepared combinatorial libraries are also available from commercial sources (e.g., ChemRx, South San Francisco, Calif.).

There are known methods for detecting, identifying, or screening for hypocretin agonists or antagonists. Typically, such methods rely on the observation that activation of hypocretin receptor is associated with an increase in intracellular calcium ([$Ca^{2+}$]) concentrations (Smart et al., Br. J. Pharmacol. 129(7):1289-91 (2000); Kukkonen et al., Neuroreport 12(9):2017-20 (2001); and Lund et al., J. Biol. Chem. 275 (40):30806-12 (2000)).

One procedure involves cell lines such as Chinese hamster ovary-K1 cells, and includes a first set of cells that are transfected with hypocretin receptors, and a second set of cells that are not transfected with hypocretin receptors. Each of the first and second sets of cells are evaluated to determine their response to hypocretin or a known agonist thereof. Further, each of the first and second sets of cells are evaluated to determine their response to a test compound. It is assumed that in response to hypocretin or a known agonist thereof, the transfected cells will show a greater response than the non-transfected cells. The test compound is evaluated as to whether it shows a activity profile similar to that of hypocretin or the known agonist. The table below illustrates possible outcomes of this procedure.

|      |                    | test compound | hypocretin or known agonist |
|------|--------------------|---------------|-----------------------------|
| Neg. | nontransfected cell | no response   | no response                 |
|      | transfected cell    | no response   | response                    |
| Pos. | nontransfected cell | no response   | no response                 |
|      | transfected cell    | response      | response                    |

In the first trial, the hypocretin or known agonist thereof shows a response in the transfected cell, but not in the non-transfected cell, as expected. Because the test compound shows no response in either of the sets of cells, the result is negative: the test compound is not a hypocretin agonist. In the second trial, because the test compound shows an activity profile similar to the hypocretin or known agonist thereof, the result is positive: the test compound is a hypocretin agonist.

Many of these assay procedures use calcium imaging, although other methods are available. For example, assays that measure changes in the cell membrane potential can be used. Related approaches include current clamp and voltage clamp techniques. These assays can be performed in association with manipulation of a bathing medium to determine which ionic currents are affected by a substance. Likewise, a wide variety of other techniques exist for assessing the biological effects of test molecules in relation to those of hypocretin or known agonists thereof. Further, in addition to Chinese hamster ovary-K1 cells, other cell lines can be used, such as neurons cultured from rat medial and lateral hypothalamus (van den Pol et al., J. Neurosci. 18(19):7962-71 (1998)) and spinal cord (van den Pol, J. Neurosci. 19(8):3171-82 (1999)).

Hypocretin agonists and antagonists may also be identified using structural analysis. Recent studies indicate that certain regions of the hypocretin polypeptide are important for ligand-receptor interaction (Darker et al., Bioorg. Med. Chem. Lett. 11(5):737-40 (2001)). Relatedly, computer aided drug design can be used in the evaluation or development of test compounds with regard to their hypocretin agonist activity. Computer programs such as Dock, Frodo, and Insight can be used to aid in the design and development of peptides, peptidomimetics, and small molecules that interact with the hypocretin receptor.

3. Weight Disorders

A. General

There are a number of disorders that affect the weight or body composition of an individual, causing the individual to seek prophylactic or therapeutic treatment. The term weight disorder refers to an acute or chronic condition or disease in which the individual has excess body weight in an amount sufficient to cause concern to the individual, their medical advisor, or nutritional counselor. Weight disorders can be multifactorial, often involving one or more social, behavioral, cultural, psychological, metabolic, biochemical, physiological, neurologic, endocrinologic, or genetic factors. Weight disorders are usually based on a sign of excess body weight. These signs may be the body mass index, waist circumference, waist to hip ratio, skin fold thickness, body density, body weight, or body fat percentage of the individual. Common examples of a weight disorder include obesity and overweight. Weight disorders such as those discussed below can be prevented or treated by the methods described herein.

B. Obesity and Overweight

The term overweight refers to a weight disorder in which an individual's body weight is in excess of their ideal body weight, yet the condition is not as severe as obesity. One common definition of overweight is a body mass index of 25 to 29.9 kg/m$^2$.

The term obesity refers to a weight disorder in which an individual's body weight is in excess of their ideal body weight. This disorder is more severe than overweight. One common definition of obesity is a body weight that is 20 percent over an ideal body weight, and the individual has an excess amount of body fat. In another definition, obesity is defined as the top 15 percent of the population's weight for a given height. Another common definition of obesity is a body fat percentage that exceeds 5% of the average percentage for the individual's age and sex classification. For example, young women may be considered obese when body fat is 25% or greater and middle-aged women may be considered obese when body fat is 30% or greater. Similarly, young men may be considered obese when body fat is 20% or greater and middle-aged men may be obese when body fat is 30% or greater. Yet another definition of obesity is a body fat percentage of >25% for men and >30% for women. Another definition of obesity is a body mass index (BMI) of 30 kg/m$^2$ or higher. Other definitions of obesity have further divided the upper range of BMI scores into obesity and morbid obesity, wherein a score of 30 to 40 is obese, and a score greater than 40 is morbidly obese. Still another definition divides obesity into three classes: a BMI of 30 to 34.9 as obesity class I obesity, 35 to 39.9 as obesity class II, and 40 or more as severe obesity class III. Another definition of obesity is an excess of body fat, which frequently results in a significant impairment of health. Morbid obesity can be defined as a severe degree of obesity wherein excessive body fat causes or exacerbates other serious and life threatening illnesses known as co-morbidities.

4. Patients Amenable to Treatment

Individuals amenable to prevention or treatment include individuals who are presently asymptomatic but who are at risk of developing a weight disorder, e.g., obesity or overweight, at a later time. Such individuals include those having relatives who have experienced a weight disorder, and those whose risk is determined by analysis of genetic or biochemical markers, or by biochemical methods. Other individuals amenable to prevention or treatment can include individuals wherein the administration of the treatment ameliorates, prevents, or reduces one or more signs of excess body weight within hours or months or treatment. Individuals to receive treatment can also include individuals who are not diagnosed with any weight disorder, including those individuals desiring or requiring a reduction in excess body weight for cosmetic or other reasons. Individuals amenable to treatment may or may not be free of narcolepsy.

Genetic markers of risk for developing a weight disorder have been determined. For example, the HMGIC gene has been implicated as playing a role in fat cell proliferation (Anand et al., Nat. Genet. 24(4):377-380 (2000)). It has also been reported that primiparous homozygous carriers of the G protein beta 3 825 TT allele are at high risk for obesity and post-pregnancy weight retention if they do not exercise regularly (Gutersohn et al., Lancet 355(9211):1240-1241 (2000)). The MC4R gene is another gene believed to play a significant role in regulating feeding behavior and body weight in humans and other mammals (Kim et al., Mamm. Genome 11(2):131-135 (2000)). Similarly, the mahogany gene has been implicated in obesity (Nagle et al., Nature 398(6723): 148-152 (1999). In another example, others have suggested that the urocortin gene a candidate gene for susceptibility to obesity (Delpanque et al., J. Clin. Endocrinol. Metab. 87(2): 867-869 (2002)). Others have indicated that variations in the ADRB2 gene and LEPR gene may contribute to susceptibility to weight gain (van Rossum et al., Int. J. Obes. Relat. Metab. Disord. 26(4):517-528 (2002)).

Biochemical markers of risk can include a defect in the proteolytic processing of the prepro-orexin precursor of the known hypocretin (orexin) molecules, or in the posttranslational modification mechanism that results in the abnormal production of Hcrt-1 (orexin-A) and Hcrt-2 (orexin-B) molecules. Another biochemical markers of risk for weight disorders is low density lipoprotein subclass phenotype B (Brunzell et al., Molecular and Genetic Aspects of Obesity, vol. 5, Pennington Center Nutrition Series, edited by Bray et al., Baton Rouge and London, Louisiana State University Press, 1996, pp. 355-363). Yet another biochemical marker is serum insulin-like growth factor-binding protein-1 (IGFBP-1) measurements. Low IGFBP-1 levels have been associated with obesity (Lee et al., Proc. Soc. Exp. Biol. Med. 216(3):319-57 (1997)). Elevated plasma leptin concentrations among overweight men have been proposed as a marker of leptin resistance and subsequent weight gain (Chu et al., Int. J. Obes. Relat. Metab. Disord. 25(3):346-353 (2001)). Other metabolic abnormalities associated with obesity have been reported (Williams et al., Ann. Med. 24(6):469-75 (1992)).

In asymptomatic individuals, treatment of weight disorders can begin at any age including antenatally, or at birth. For example, in obesity, if a biochemical marker of disease, is detected, treatment should usually begin shortly thereafter. Similarly, if the likelihood of developing a weight disorder is based on relatives having the disease or on detection of a genetic or biochemical marker, treatment can also be administered shortly after identification of these risk factors, or shortly after diagnosis. Alternatively, an individual found to possess a genetic or biochemical marker can be left untreated but subjected to regular monitoring for biochemical or symptomatic changes without treatment. The decision whether to treat immediately or to monitor symptoms depends in part on the extent of risk predicted by the marker(s) found in the individual for a particular weight disorder. Once begun, a prophylactically or therapeutically effective dosage regime of hypocretin is typically continued at intervals for a period of a week, a month, three months, six months or a year. In some individuals, treatment is administered for up to the rest of a individual's life. Treatment or prophylaxis can generally be stopped if a biochemical risk marker disappears or diminishes to normal parameters.

Other individuals amenable to treatment show or have shown behavioral symptoms of a weight disorder, such as inactivity, overeating, or high calorie food selection. Such symptoms can be detected by any of a variety of techniques, including self observation, observation by a third party, diaries, logs, and the like. In addition, symptomatic individuals often have biochemical or genetic risk factors as described for asymptomatic individuals. In symptomatic patients, treatment usually begins at or shortly after diagnosis of symptoms. Treatment is typically continued at intervals for a week, a month, six months, a year or up to the rest of the patient's life. Typically, the individual's symptoms are monitored. If monitoring indicates a sustained reduction or elimination of symptoms for a period of at least a month, and preferably at least three months, treatment can be terminated or reduced in dosage. Monitoring is continued and treatment is resumed if symptoms reappear or worsen. If treatment causes no significant amelioration of symptoms in an individual for a period of at least six months, and typically at least one year, or if the side effects of the treatment are intolerable to an individual, then treatment can be discontinued.

Another group of individuals amenable to prophylaxis or treatment include individuals who are presently asymptomatic but who are at risk for developing a deficiency in motor or muscular activity, such as fatigue and depression.

Fatigue is usually described as a feeling of lack of energy, weariness, or tiredness. Fatigue is also commonly referred to as exhaustion or lethargy. Fatigue can be a nonspecific symptom of a psychological or physiologic disorder. For example, fatigue may be associated with fibromyalgia, depression, chronic fatigue syndrome, or seasonal affective disorder. In other cases, fatigue is related to boredom, unhappiness, disappointment, lack of sleep, or hard work. Such individuals amenable to prophylaxis or treatment include those having relatives who have experienced a fatigue or depression condition, and those whose risk is determined by analysis of genetic or biochemical markers, or by biochemical methods. Other individuals amenable to prevention or treatment can include individuals wherein the administration of the treatment ameliorates, prevents, or reduces one or more signs of fatigue or depression within hours or months or treatment. Individuals to receive treatment can also include individuals who are not diagnosed with any fatigue or depression condition disorder, including those individuals desiring or requiring a reduction in fatigue or depression for any other reason. Individuals amenable to treatment may or may not be free of narcolepsy.

Genetic markers of risk for developing a motor or muscular activity condition such as fatigue have been suggested in the literature (Urnovitz et al., Clin. Diagn. Lab. Immunol. 6(3):330-5 (1999); Yunus et al., J. Rheumatol. 26(2):408-12 (1999)). Biochemical markers of motor or muscular activity conditions, such as reduced intracellular concentrations of ATP, have also been suggested for fatigue (Wong et al., Chest 102(6):1716-22 (1992)). Similarly, Yoshikawa et al. suggest genetic markers for depression (Genome Res. 12(3):357-366 (2002)) and Young et al. report biochemical markers for depression (Am. J. Psychiatry 159(7):1237-1239 (2002)).

In asymptomatic individuals, treatment of motor or muscular activity disorders can begin at any age including antenatally, or at birth. For example, in motor or muscular activity conditions, if a biochemical marker of the condition is detected, treatment should usually begin shortly thereafter. Similarly, if the likelihood of developing a motor or muscular disorder is based on relatives having the disease or on detection of a genetic or biochemical marker, treatment can also be administered shortly after identification of these risk factors, or shortly after diagnosis. Alternatively, an individual found to possess a genetic or biochemical marker can be left untreated but subjected to regular monitoring for biochemical or symptomatic changes without treatment. The decision whether to treat immediately or to monitor symptoms depends in part on the extent of risk predicted by the marker(s) found in the individual for a particular muscular or motor activity disorder. Once begun, a prophylactically or therapeutically effective dosage regime of hypocretin is typically continued at intervals for a period of a week, a month, three months, six months or a year. In some individuals, treatment is administered for up to the rest of a individual's life. Treatment or prophylaxis can generally be stopped if a biochemical risk marker disappears or diminishes to normal parameters.

Another group of individuals amenable to prophylaxis or treatment include individuals who are presently asymptomatic but who are at risk for developing a deficiency in metabolism, such as that which is associated with hypothyroidism or adult growth hormone deficiency (Jorgensen et al., Horm. Res. 42(4-5):235-41 (1994)).

Such individuals include those having relatives who have experienced a metabolism disorder, and those whose risk is determined by analysis of genetic or biochemical markers, or by biochemical methods. Other individuals amenable to prevention or treatment can include individuals wherein the administration of the treatment ameliorates, prevents, or reduces one or more signs of a metabolism disorder within hours or months or treatment. Individuals to receive treatment can also include individuals who are not diagnosed with any metabolism disorder, including those individuals desiring or requiring an increase in metabolism for other reasons. Individuals amenable to treatment may or may not be free of narcolepsy.

Genetic markers of risk for developing a metabolism disorder have been determined. For example, hair analysis has been suggested as a genetic marker for hypothyroidism (Lin et al., Ultrastruct. Pathol. 25(5):357-60 (2001)). Biochemical markers of risk for metabolism order have been determined. For example, serum concentrations of IGF-1 and IGFBP-3 have been suggested as markers for growth hormone deficient individuals (Jaruratanasirikul et al., J. Med. Assoc. Thai. 83(6):619-626 (2000)). Likewise, serum concentrations of TSH have been suggested as markers for hypothyroidism (Siklar et al., J. Pediatr. Endocrinol. Metab. 15(6):817-21 (2002)).

In asymptomatic individuals, treatment of metabolic disorders can begin at any age including antenatally, or at birth. For example, in obesity, if a biochemical marker of disease, is detected, treatment should usually begin shortly thereafter. Similarly, if the likelihood of developing a metabolic disorder is based on relatives having the disease or on detection of a genetic or biochemical marker, treatment can also be administered shortly after identification of these risk factors, or shortly after diagnosis. Alternatively, an individual found to possess a genetic or biochemical marker can be left untreated but subjected to regular monitoring for biochemical or symptomatic changes without treatment. The decision whether to treat immediately or to monitor symptoms depends in part on the extent of risk predicted by the marker(s) found in the individual for a particular metabolic disorder. Once begun, a prophylactically or therapeutically effective dosage regime of hypocretin is typically continued at intervals for a period of a week, a month, three months, six months or a year. In some individuals, treatment is administered for up to the rest of a individual's life. Treatment or prophylaxis can generally be stopped if a biochemical risk marker disappears or diminishes to normal parameters.

Another group of individuals amenable to treatment include individuals who are at risk for developing any of a number of weight-related conditions. Examples of weight related conditions of the pulmonary system include obstructive sleep apnea, obesity hypoventilation syndrome, asthma, reactive airway disease, and shortness of breath. Examples of weight related conditions of the cardiovascular system include high blood pressure or hypertension, cardiovascular disease, coronary artery disease or atherosclerosis, elevated cholesterol and triglycerides, hyperlipidemia, and Cor Pulmonale caused by pulmonary hypertension. Examples of weight related conditions of the gastrointestinal system include gastroesophageal reflux disease, reflux esophagitis, recurrent heartburn, urinary stress incontinence, recurrent ventral hernias, gout, gallbladder disease, and gallstones. Examples of weight related conditions of the endocrine system include diabetes, menstrual irregularity or infertility, hirsutism, hyperlipidemia, and hypercholesterolemia. Examples of weight related conditions of the genitourinary and reproductive systems include frequent urinary tract infections, stress urinary incontinence, irregular menses, and infertility. Examples of weight related conditions of the musculoskeletal system include degeneration of knees and hips, disc herniation, joint pain, osteoarthritis, and chronic back pain. Other weight related conditions include multiple skin disorders, which are most frequently related to diabetes and difficulty with hygiene. Further, depression can be caused or worsened by a weight condition. Still further weight related conditions include certain types of cancer such as cancer of the breast, endometrium, colon, and prostate.

5. Diagnostic and Monitoring Methods

A. Diagnosing and Monitoring Excess Body Weight

Signs of excess body weight can be detected or monitored by any one or a number of various methods including body mass index, waist circumference, waist to hip ratio, skin fold thickness, body density, body weight, or body fat percentage of the individual. Body fat percentage can be determined by skin fold thickness, bioelectrical impedance, hydrostatic weighing, ultrasound, total body electrical conductivity, or dual emission x-ray absorptiometry. The diagnosing or monitoring can include maintaining a log of the signs, whereby the signs are evaluated over a selected period of time.

Skin fold thickness refers to a method for determining body fat that involves measurements from different areas of the body, such as the triceps, shoulder blades, and hips. Often, these measurements are made with skin fold calipers that measure the thickness of the skin. Estimated body fat content or percentage is then calculated with a standardized formula based on the thickness measurements.

Bioelectrical impedance (BIA) is a method for determining body fat that involves the use of a handheld instrument called an impedance analyzer that transmits a non-invasive low frequency electrical current through electrodes placed on an individual's hand and/or foot. Typically, a gel is used to facilitate transmission of the current between the instrument and the body. The instrument determines the body's resistance to electrical current, and estimated body fat content or percentage is calculated based on the measured resistance.

Hydrostatic weighing is another method for determining body fat content. In this method, the individual expels as much air as possible from their lungs, and is submerged into a pool or tank of water. The submerged individual is then weighed, and the underwater weight is compared with the dry-land weight to determine body density. Because density is inversely proportional to the percentage of body fat, the greater the body's density, the lower the body fat percentage.

Ultrasound is another method for determining body fat content. In this method, an ultrasound device is held against the skin at various sites of the body, and sound is sent through the surface to measure subcutaneous thicknesses, such as the distances between skin, fat, and muscle layer. Body fat content is determined based on these measurements.

Total body electrical conductivity (TOBEC) is another method for determining body fat content, and is based on the principle that lean tissue conducts electricity more effectively than fat. In this method, the individual is passed through a standing electromagnetic field. As the individual passes through the field, the strength of the field is altered in relation to the electrolytes found in the body water. Body water is a constant proportion of lean tissue, so this reading allows for the estimation of lean body mass. Body fat content is then determined based on the lean body mass.

Dual emission X-ray absorptiometry (DEXA) is another method for determining body fat content. This method uses a very low-dose X-ray scan to measure the density of the body tissues. Body fat content is then determined based on the density measurements.

B. Diagnosing and Monitoring Motor and Muscular Activity Levels

The motor or muscular activity level of the individual can be measured by a variety of means. Motor activity levels may be directly observed and measured by clinicians, or the individual may themselves measure their activity level which typically includes body movement or locomotion. The monitoring can include maintaining a log of activity, including intensity and duration of the activity. An actigraph device, or activity monitor, may be used. An actigraph detects activity by sensing motion via an internal accelerometer. It is a small lightweight instrument that can be worn, for example, on the wrist, waist, or ankle to record physical activity. Actigraphs are often used to estimate energy expenditure or to study motion in an individual, as described in Example 4 and shown in FIG. 1.

Muscular activity can be measured with an electromyograph, in a process known as electromyography (EMG). This procedure measures the electrical currents generated in a muscle during its contraction C. Diagnosing and Monitoring Metabolism Levels The metabolism level of an individual can be measured in a variety of ways. One method of determining metabolism, or energy expenditure, in an individual involves continuous measurements of heat output (direct calorimetry) or exhaled gas exchange (indirect calorimetry) through the use of a metabolic chamber. An individual remains in the room-like chamber for a certain period of time (e.g. 24 hours), during which time their metabolic rate is measured. In direct calorimetry, measurements are taken of the heat released from the individual's body to determine how much energy the individual has burned. In indirect calorimetry, oxygen consumption, carbon dioxide production and nitrogen excretion are measured to calculate a ratio that reflects energy expenditure. Both measurements can indicate the individual's metabolic rate.

Free-living analysis is another method of measuring the metabolism level of an individual. This method relies on monitoring the heart rate of the individual and maintaining an activity diary or log. These measures are used to compute energy expenditure which is a component of metabolism.

D. Diagnosing and Monitoring Hypocretin Levels

A hypocretin radioimmunoassay (RIA) can be used for diagnostic and monitoring purposes, through analysis of hypocretin in cerebrospinal fluid (CSF) and plasma. These assays can be used to evaluate changes in the hypocretin system. Nishino et al. discuss such assays in Lancet 355:39-40 (2000). The radioimmunoassays involve competition of $^{125}$I-hypocretin and standard or test samples for limited quantities of hypocretin-specific antibody. If the standard or test sample contains a lower amount of hypocretin, then a higher amount of $^{125}$-hypocretin can bind to the antibody. Conversely, if the standard or test sample contains a higher amount of hypocretin, then a lower amount of $^{125}$I-hypocretin can bind to the antibody. Standard curves can be constructed by measuring the amount of bound $^{125}$I-hypocretin as a function of hypocretin in a standard reaction. The concentration of hypocretin in a test sample can then be determined using the standard curve. Assay kits such as these are commercially available (e.g. Phoenix Pharmaceuticals, 530 Harbor Blvd, Belmont, Calif. USA).

Figure 2:
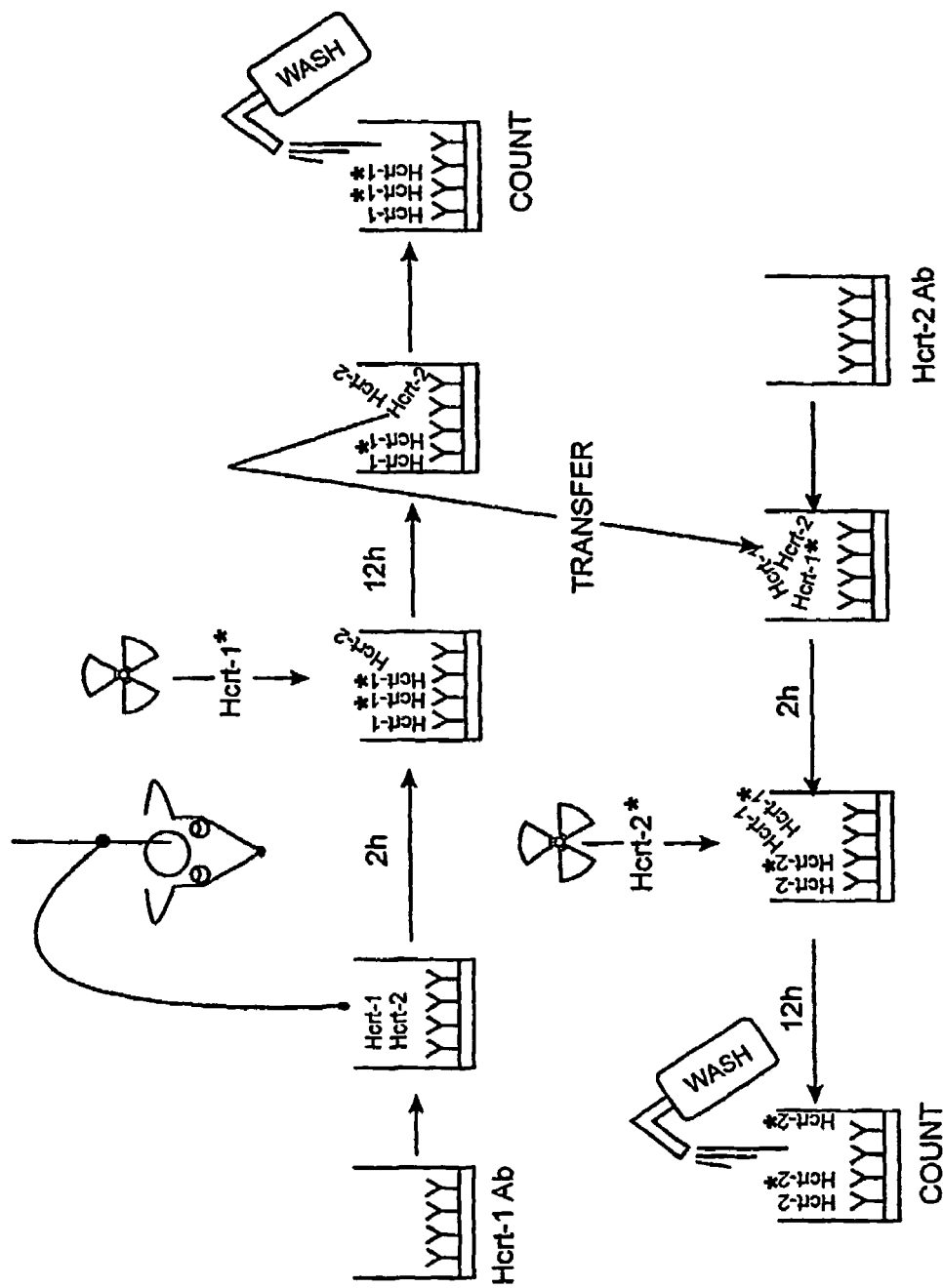
FIG. 2. The protocol for a sequential multiple antigen radioimmunoassay for hypocretin-1 (Hcrt-1) and hypocretin-2 (Hcrt-2). Sample or standard is loaded into wells onto which antiserum for Hcrt-1 has been pre-adsorbed via protein-A Subsequently, radiolabeled Hcrt-1 (Hcrt-1*) is added to the wells. Competition for the antiserum then ensues between Hcrt-1 and Hcrt-1*. The contents of the wells are then transferred to new wells onto which antiserum for Hcrt-2 has been preadsorbed and the procedure repeated but with radiolabeled Hcrt-2 (Hcrt-2*). The previous wells are washed and counted for bound radioactivity.

A modified solid-phase radioimmunoassay (RIA) can also be used for diagnostic and monitoring purposes. As described in Example 5 and shown in FIG. 2, a solid-phase RIA can be used for measurement of hypocretin in cerebrospinal fluid (CSF) and plasma. The presence, absence, or change in hypocretin levels in CSF or plasma can indicate changes in the Hcrt system.

The above tests work by comparing a measured level of hypocretin in a patient with a baseline level determined in a control population of patients unaffected by a particular weight disorder. A significant departure between the measured level in a patient and baseline levels in unaffected persons signals a positive outcome of the test. A departure is considered significant if the measured value falls outside the range typically observed in unaffected individuals due to inherent variation between individuals and experimental error. For example, a departure can be considered significant if a measured level does not fall within the mean plus one standard deviation of levels in a control population. In some methods, a departure between a measured level and control levels is judged significant if the measured level is at least the level of the, 75th, 80th or 95th percentile of a control population. In other words, the measured level in the patient occurs in only 50%, 25%, 20% or 5% of normal individuals. If the measured level of Hcrt-1 or Hcrt-2 does not differ significantly from baselines levels in a control population, the outcome of the diagnostic test is considered negative.

Depending on the particular procedure used, hypocretin can be directly labeled as with isotopes, chromophores, lumiphores, chromogens, or indirectly labeled such as with biotin to which a streptavidin complex can later bind. Hypocretin can also be unlabeled.

Hypocretin system deficiencies can also be evaluated based on polymorphism studies. For example, nucleic acid from a test subject is compared to nucleic acid reference to determine whether the test subject has a sequence different from that of the reference. Differences in sequence can indicate a polymorphism in the hypocretin peptide. Hypocretin polymorphisms have been reported (Gencik et al., Neurology 56(1):115-7 (2001)).

E. Diagnosing Hypocretin Receptor Deficiency

Hypocretin receptor deficiency can be evaluated based on polymorphism studies. For example, nucleic acid from a test subject is compared to nucleic acid reference to determine whether the test subject has a sequence different from that of the reference. Differences in sequence can indicate a polymorphism in the receptor. Hypocretin receptor polymorphisms have been reported (Lin et al. Cell 98(3):365-376 (1999)).

6. Treatment Regimes

The invention also provides methods of administering a prophylactically or therapeutically effective dosage regime of hypocretin or an agonist thereof to an individual for treatment or prophylaxis weight disorders such as obesity and overweight, as well as for the treatment or prophylaxis of muscular or motor activity deficiencies, and metabolic disorders.

In therapeutic applications, compositions or medicants are administered to a individual suffering from a weight disorder such as obesity or overweight, until there is a reduction in excess body weight. The compositions or medicants can also be administered to an individual suffering from a muscular or motor activity disorder or metabolic condition, until there is an amelioration of or improvement in the disorder or condition.

In prophylactic applications, compositions or medicants are administered to a individual at risk for suffering from a weight disorder such as obesity or overweight, to reduce the possibility of the individual suffering from the weight disorder, or to prevent the individual from gaining further excess body weight. The compositions or medicants can also be administered to an individual at risk for suffering from a muscular or motor disorder or metabolic condition, to reduce the possibility of the individual suffering from the disorder or condition, or to prevent the disorder or condition from progressing.

In therapeutically and prophylactically effective regimes, hypocretin can be administered in several dosages until a sufficient response has been achieved. The treatment or prophylaxis can be monitored and repeated dosages can be given. Hypocretin may or may not be labeled.

The amount of hypocretin that can be combined with a carrier material to produce a single dosage form vary depending upon the disease treated, the type of drug, the mammalian species, and the particular mode of administration. As a general guide, suitable unit doses for hypocretin of the present invention, for example, can contain between about 0.3 µg/kg to about 2.5 µg/kg. Another exemplary unit dose corresponds to between about 0.05 µg/kg to about 10 µg/kg, depending on the individual. Such unit doses can be administered more than once a day, for example 1, 2, 3, 4, 5 or 6 times a day, so that the total daily dosage for a 70 kg adult is in the range of about 21 µg to about 4200 µg. In other treatment regimes, the total daily dosage for a 70 kg adult is in the range of about 2.1 µg to about 42 mg.

Such unit doses can also be administered every 24 hours. Some such unit doses can also be administered at least every 12 hours. A typical dosage can be a 210 µg tablet taken once a day, or, multiple times per day (for example, a 105 µg tablet taken twice per day), or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release. Such therapy can extend for a number of weeks or months, and in some cases, years.

The specific dose level for any particular patient can depend on a variety of factors including the activity of the specific compound employed; the age, body weight, general health, sex and diet of the individual being treated; the time and route of administration; the rate of metabolism or excretion; other drugs which are concurrently or have previously been administered; and the severity of the particular disease undergoing therapy. In some instances, dosages outside the above ranges are used to interrupt, adjust, or terminate treatment in conjunction with individual patient response.

For therapeutically or prophylactically effective dosage regimes of hypocretin used in the methods of the present invention, a therapeutically or prophylactically effective dose for humans can be estimated initially from non-human animal models.

Toxicity and therapeutic efficacy of the compounds described herein can be determined by standard pharmaceutical procedures in experimental animals, e.g., by determining the $LD_{50}$, (the dose lethal to 50% of the population tested) and the $ED_{50}$ (the dose therapeutically effective in 50% of the population tested). The dose ratio between toxic and therapeutic effect is the therapeutic index-and can be expressed as the ratio between $LD_{50}$ and $ED_{50}$. Compounds which exhibit high therapeutic indices are preferred. The data obtained from these nonhuman animal studies can be used in formulating a dosage range that is not toxic for use in humans. The dosage of such compounds lies preferably within a range of circulating concentrations that include the $ED_{50}$ with little or no toxicity. The exact formulation, route of administration, and dosage can be chosen by the individual physician in view of the patient's condition. (See, e.g., Fingi et al. (1975) In: *The Pharmacological Basis of Therapeutics*, Ch. 1).

7. Pharmaceutical Compositions and Methods of Administration

Hypocretin or an agonist thereof can be delivered or administered to a mammal, e.g., a human patient or subject, alone, in the form of a pharmaceutically acceptable salt or hydrolyzable precursor thereof, or in the form of a pharmaceutical composition wherein the compound is mixed with suitable carriers or excipient(s) in a therapeutically effective amount. A therapeutically effective regime means that a drug or combination of drugs is administered in sufficient amount and frequency and by an appropriate route to at least detectably reduce, prevent, delay, inhibit, or reverse development of at least one sign, symptom, or biochemical marker of excess body weight or a weight disorder. A "prophylactically effective amount," "therapeutically effective amount," "pharmacologically acceptable dose," or "pharmacologically acceptable amount" means that a sufficient amount of hypocretin, or agonist thereof, or combination of hypocretin with other agents is present to achieve a desired result, e.g., reducing, preventing, delaying, inhibiting, or reversing a sign, symptom, or biochemical markers of excess body weight or a sleep disorder when administered in an appropriate regime. In a preferred embodiment, a sufficient amount of hypocretin or agonist thereof is present to reduce, prevent, delay, inhibit, or reverse a sign, symptom, or biochemical markers of excess body weight or a weight disorder or the progression of excess body weight or a weight disorder when administered in an appropriate regime.

Hypocretin and other active agents that are used in the methods of the present invention can be administered as pharmaceutical compositions comprising hypocretin or the active agent, together with a variety of other pharmaceutically acceptable components. Pharmaceutical compositions can be in the form of solids (such as powders, granules, dragees, tablets, or pills), semi-solids (such as gels, slurries, or ointments), liquids, or gases (such as aerosols or inhalants).

Suitable formulations for use in the present invention are found in *Remington's Pharmaceutical Sciences* (Mack Publishing Company (1985) Philadelphia, Pa., 17$^{th}$ edition) and Langer, *Science* (1990) 249:1527-1533, which are incorporated herein by reference. The pharmaceutical compositions described herein can be manufactured in a conventional manner, i.e., mixing, dissolving, granulating, dragee-making, levigating, emulsifying, encapsulating, entrapping, or lyophilizing processes.

In preparing the formulations of the present invention, pharmaceutically recognized equivalents of each of the compounds can be alternatively used. These pharmaceutically recognized equivalents can be pharmaceutically acceptable salts or pharmaceutically acceptable acid addition salts.

A pharmaceutically acceptable salt is a non-toxic alkali metal, alkaline earth metal, or an ammonium salt commonly used in the pharmaceutical industry including a sodium, potassium, lithium, calcium, magnesium, barium, ammonium, and protamine zinc salt, which is prepared by methods well known in the art. The term also includes a non-toxic acid addition salt, which is generally prepared by reacting the compounds of the present invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt which retains the biological effectiveness and properties of the free bases and which is not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like (see, e.g., Bundgaard, H., ed., *Design of Prodrugs* (Elsevier Science Publishers, Amsterdam 1985)).

Hypocretin and other active agents can be formulated with common excipients, diluents, or carriers, and compressed into tablets, or formulated as elixirs or solutions for convenient oral administration. Hypocretin and other active agents can also be formulated as sustained release dosage forms and the like.

The invention provides methods for administering a therapeutically effective dosage regime of hypocretin and other active compounds of the invention to a peripheral tissue in a patient (i.e., tissues other than central nervous system tissues). This can be achieved in various ways, including oral, buccal, rectal, parenteral, intraperitoneal, intradermal, transdermal, intratracheal, and intramuscular administration. Moreover, hypocretin and other active agents can be administered in a local rather than systemic manner, in a depot or sustained release formulation. In addition, hypocretin and other active agents can be administered in a liposome. In some methods of the invention, additional agents may be administered to facilitate the passage of hypocretin and other active compounds across the blood brain barrier.

For injection, hypocretin along with other active agents of the invention can be formulated into preparations by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. Preferably, for injection, the compounds of the present invention can be formulated in aqueous solutions, preferably in physiologically compatible buffers such as Hanks's solution, Ringer's solution, or physiological saline buffer. For ansmucosal administration, penetrants appropriate to the barrier to be permeated are used in the formulation. Such penetrants are generally known in the art.

For oral administration, the hypocretin along with other active agents can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in a conventional manner.

For administration by inhalation, the compounds for use according to the present invention are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Hypocretin and other active agents of the invention can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oil-based or aqueous vehicles, and can contain formulator agents such as suspending, stabilizing and/or dispersing agents. The compositions are formulated as sterile, substantially isotonic and in full compliance with all Good Manufacturing Practice (GMP) regulations of the U.S. Food and Drug Administration.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Hypocretin and other active agents can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In some methods, long-circulating, i.e., stealth, liposomes can be employed. Such liposomes are generally described in Woodle, et al., U.S. Pat. No. 5,013,556, the teaching of which is hereby incorporated by reference. The compounds of the present invention can also be administered by controlled release means and/or delivery devices such as those described in U.S. Pat. Nos. 3,845,770; 3,916,899; 3,536,809; 3,598,123; and 4,008,719; the disclosures of which are hereby incorporated by reference.

Certain organic solvents such as dimethylsulfoxide (DMSO) also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The therapeutically effective amounts for the methods of the present invention can depend on the subject being treated, on the subject's weight, the subject's overall health, the severity of the affliction, the manner of administration and the judgment of the prescribing physician or other medical advisor.

8. Kits

The invention further provides kits comprising hypocretin. Usually, the kit also contains instructions for carrying out the methods of the invention.

9. REFERENCES

De Lecea L, Kilduff T, Peyron C, Gao X B, Foye P E, Danielson P E, Fukahara C, Battenberg E L F, Gautvik V T, Barlett F S, Frankel W N, van den Pol A N, Bloom F, Gautvik K M, Sutcliffe J G (1998) The hypocretins: Hypothalamus-specific peptides with neuroexcitatory activity. Proc Natl Acad Sci USA 95:322-327.

Dube M G, Kalra S P, Kalra P S (1999) Food intake elicited by central administration of orexins/hypocretins: identification of hypothalamic sites of action. Brain Res 842:473-477.

Edwards C M, Abusnana S, Sunter D, Murphy K G, Ghatei M A, Bloom S R (1999) The effect of the orexins on food intake: comparison with neuropeptide Y, melanin-concentrating hormone and galanin. J Endocrinol. 160:R7-12.

Hara J, Beuckmann C T, Nambu T, Willie J T, Chemelli R M, Sinton C M, Sugiyama F, Yagami K, Goto K, Yanagisawa M, Sakurai T (2001) Genetic ablation of orexin neurons in mice results in narcolepsy, hypophagia, and obesity. Neuron 30:345-354.

Ida T, Nakahara K, Katayama T, Murakami N, Nakazato M (1999) Effect of lateral cerebroventricular injection of the appetite-stimulating neuropeptide, orexin and neuropeptide Y, on the various behavioral activities of rats. Brain Res 821:526-529.

John J, Wu M F, Siegel J M (2000) Systemic administration of hypocretin-1 reduces cataplexy and normalizes sleep and waking durations in narcoleptic dogs. Sleep Res.Online 3:23-28 http://www.sro.org/2000/John/23/.

Kiyashchenko L I, Mileykovskiy B Y, Lai Y Y, Siegel J M (2001) Increased and decreased muscle tone with orexin (hypocretin) microinjections in the locus coeruleus and pontine inhibitory area. J Neurophysiol. 85:2008-2016.

Levitt D R, Teitelbaum P (1975) Somnolence, akinesia, and sensory activation of motivated behavior in the lateral hypothalamic syndrome. Proc Natl Acad Sci U.S.A 72:2819-2823.

Lin L, Faraco J, Kadotani H, Rogers W, Lin X, Qui X, de Jong P, Nishino S, Mignot E (1999) The REM sleep disorder canine narcolepsy is caused by a mutation in the hypocretin (orexin) receptor gene. Cell 98:365-376.

Sakurai T, Amemiya A, Ishii M, Matsuzaki I, Chemelli R M, Tanaka H, Williams S C, Richardson J A, Kozlowski G P, Wilson S, Arch J R, Buckingham R E, Haynes A C, Carr S A, Annan R S, McNulty D E, Liu W S, Terrett J A, Elshourbagy N A, Bergsma D J, Yanagisawa M (1998) Orexins and orexin receptors: a family of hypothalamic neuropeptides and G protein-coupled receptors that regulate feeding behavior. Cell 92:573-585.

Schuld A, Hebebrand J, Geller F, Pollmacher T (2000) Increased body-mass index in patients with narcolepsy. Lancet 355:1274-1275.

Siegel J M (1999) Narcolepsy: A key role for hypocretins (orexins). Cell 98:409-412.

Sweet D C, Levine A S, Billington C J, Kotz C M (1999) Feeding response to central orexins. Brain Res 821:535-538.

Thannickal T C, Moore R Y, Nienhuis R, Ramanathan L, Gulyani S, Aldrich M, Comford M, Siegel J M (2000) Reduced number of hypocretin neurons in human narcolepsy. Neuron 27:469-474.

Tritos N A, Mastaitis J W, Kokkotou E, Maratos-Flier E (2001) Characterization of melanin concentrating hormone and preproorexin expression in the murine hypothalamus. Brain Res 895:160-166.

Willie J T, Chemelli R M, Sinton C M, Yanagisawa M (2001) To eat or to sleep? Orexin in the regulation of feeding and wakefulness. Annu. Rev. Neurosci 24:429-458.

Yamamoto Y, Ueta Y, Date Y, Nakazato M, Hara Y, Serino R, Nomura M, Shibuya I, Matsukura S, Yamashita H (1999) Down regulation of the prepro-orexin gene expression in genetically obese mice. Brain Res Mol Brain Res 65:14-22.

Yamanaka A, Sakurai T, Katsumoto T, Yanagisawa M, Goto K (1999) Chronic intracerebroventricular administration of orexin-a to rats increases food intake in daytime, but has no effect on body weight. Brain Res 849:248-252.

10. EXAMPLES

Example One

Hypocretin Administration Via Ventricular Injection

The effect of hypocretin administration on the body weight of a normal rat or other rodent is investigated. The study includes ten animals in the experimental group, ten animals in the control group, and ten animals in the untreated group. It is expected that this number is sufficient to demonstrate any significant effect of hypocretin on body weight in the experimental group. Animals in the experimental and control groups are fitted with an Alzet Model 2004 osmotic minipump (Alza). The minipump delivers solution to the third ventricle of the brain, adjacent to the hypothalamus, for a one to six month period. The experimental group receives hypocretin peptide continuously at dosing regimes of about 0.03 µg/kg/day to about 600 µg/kg/day. The control group receives diluent. Animals in all groups are provided with a running wheel and customary rat chow is available ad libitum. Each animal is weighed daily (or another sign of excess body weight is measured), and the running wheel activity for each animal is recorded. Administration of the hypocretin produces increased running wheel activity and decreased weight gain (or a decrease in the measured sign of excess body weight) in the experimental animals compared to the control animals and the untreated animals.

Example Two

Hypocretin Administration Via Jugular injection.

The effect of administration of hypocretin-1 or other agonists of the hypocretin receptors on rats is investigated. The study includes ten animals in the experimental group, ten animals in the control group, and ten animals in the untreated group. It is expected that this number is sufficient to demonstrate any significant effect of hypocretin-1 or other agonist on body weight in the experimental group. Animals in the experimental and control groups receive a jugular catheter implant attached to an osmotic minipump. The experimental group receives hypocretin-1 or other agonist at dosing regimes of about 0.03 µg/kg/day to about 600 µg/kg/day. The control group receives diluent. Animals in all groups are provided with a running wheel and customary rat chow is available ad libitum. Each animal is weighed daily (or another sign of excess body weight is measured), and the running wheel activity for each animal is recorded. Administration of the hypocretin or other agonist produces increased running wheel activity and decreased weight gain (or a decrease in the measured sign of excess body weight) in the experimental animals compared to the control animals and the untreated animals.

Example Three

Activity of Hypocretin in Humans

Hypocretin or hypocretin agonist is submitted to safety testing following usual Food and Drug Administration (FDA) requirements. Afterward, the effect of administration of hypocretin or hypocretin agonist on obese humans is investigated. The study includes ten humans in the experimental group and ten humans in the control group. Humans in the experimental and control groups receive administration by intranasal inhalant, or by transdermal or other means. The experimental group receives hypocretin or hypocretin agonist at dosing regimes of about 0.03 µg/kg/day to about 600 µg/kg/day for a period of four weeks. The control group receives a placebo. Activity levels of the humans in both groups are measured with a wrist actigraph, and each human is weighed daily (or another sign of excess body weight is measured).

Each animal is weighed daily, and the running wheel activity for each animal is recorded. Administration of the hypocretin produces increased running wheel activity and decreased weight gain (or a decrease in the measured sign of excess bbdy weight) in the experimental animals compared to the control animals and the untreated animals. The humans in the experimental group exhibit increased activity levels and greater weight loss (or reduction in the measured sign of excess body weight) as compared to the humans in the control group.

Example Four

Effect of Hypocretin on Activity Level

Figure 1B:
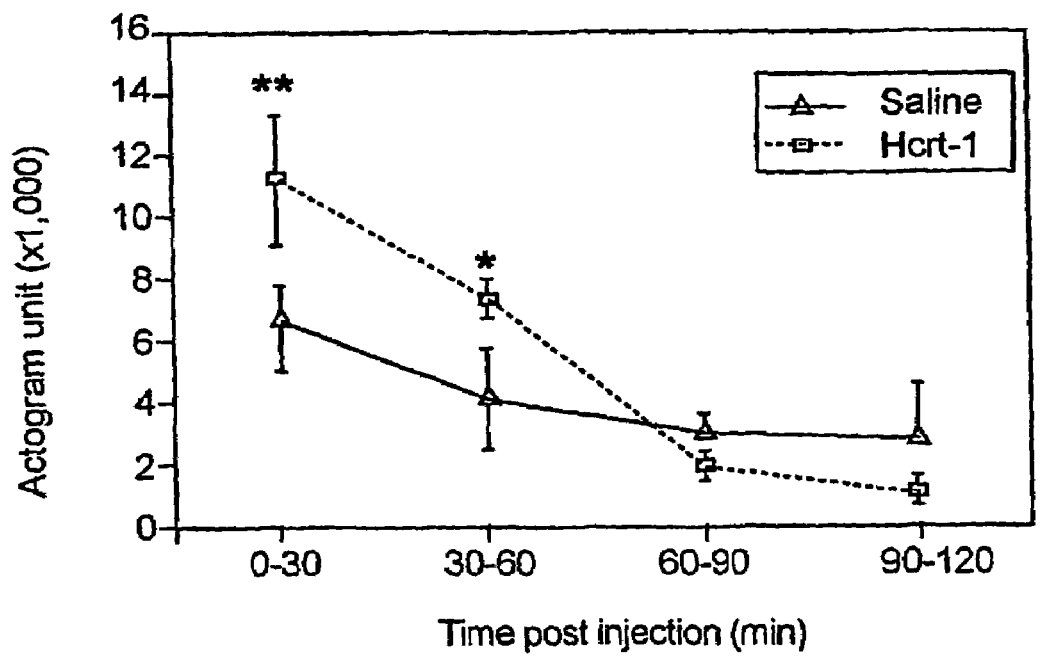

Hypocretin injection produced increased motor activity in the first 30 minutes after injection. The differences in amplitude of motor activity following hypocretin and saline injection diminished over the following 60 minutes (FIGS. 1a, 1b).

Example Five

Solid-Phase Radioimmunoassay (RIA) for Hypocretin

In order to assess the effect of the intravenous Hcrt-1 injection on central levels of the compound, cerebrospinal fluid (CSF) and blood serum was collected and analyzed after infusion of Hcrt-1. In these studies, Hcrt-1 was injected intravenously as in the behavioral studies into two Doberman pinschers, one narcoleptic, and one control that had been anesthetized with Fluothane anesthesia Saline was injected in a third dog, a non-narcoleptic control. Prior to injection and at 15, 30 min and one hour intervals after injection, CSF was collected from the cisterna magna with a spinal needle and then quickly frozen at −20. Hypocretin was extracted from 0.5-1 ml samples with reverse a phase SEP-PAK C18 column. An $^{125}$I Hcrt-1 radioimmunoassay was used to measure levels in reconstituted aliquots (described below).

In commonly used RIA procedures the competition between radiolabeled and unlabeled sample-derived peptide for the antibody takes place with all three components in solution. Separation of antibody-bound from free tracer peptide is subsequently accomplished either by precipitation of the antibodies (for example by using polyethylene glycol or a second antibody), or alternatively by adsorption of the free tracer peptide with charcoal. In addition to the time consuming nature of these separation steps (they all require incubation, centrifugation and decanting of supernatant) there is a problem of non-specific entrapment of tracer in the pellet.

In the solid-phase immunoassays previously developed for measurement of opioid peptides, neurotensin and cholecystokinin in brain microdialysates (Maidment et al., 1989; Maidment et al., 1991; Maidment and Evans, 1991), no precipitation step is required and non-specific binding is greatly reduced. Furthermore, sensitivity is increased over that obtained with more traditional methods using identical antibodies and assay volumes. In this system, the antibody is immobilized onto the surface of 96-well Immulon II-coated plates (Dynatech) through attachment of the constant region of the immunoglobulin (Ig) molecule to the purified bacterial wall protein-protein A (the use of this protein greatly increases the capacity of the wells for antibody thereby avoiding the necessity for antibody purification). Competition for the exposed antigenic sites of the antibody between labeled and unlabeled peptide is then initiated (greatest sensitivity is achieved by pre-incubation of sample or standard peptide). After a predetermined incubation period separation of bound from free tracer peptide is accomplished by simply pouring out the contents of the wells and washing with buffer. For example, the individual wells of a 96-well plate containing Ab-bound tracer peptide are then physically separated and counted in a gamma counter. This published procedure has been modified herein to enable measurement of Hcrt-1 in CSF and plasma.

The Hcrt-1, iodinated Hcrt-1, and Hcrt-1 antiserum were obtained from Phoenix Pharmaceuticals, Inc. (530 Harbor Blvd, Belmont, Calif.). Dynex Microlite 2 Plus 96-well plates (Fisher) to which is added microscint-20 (Packard) after the final wash. This enables direct reading of radioactivity in a Top Count plate reader (Packard) without the requirement to separate out individual wells. The $IC_{50}$ value for this Hcrt-1 assay is 2 fmole with a limit of detection of 0.1 fmole.

Apart from the advantages of convenience and sensitivity afforded by this method, another significant advance originates from the negligible non-specific binding associated with the use of the plates. This characteristic enables the transfer of individual well contents prior to the final wash (i.e., sample plus iodinated peptide) into wells containing immobilized antibody to a second peptide. In this way it is possible to sequentially assay several different peptides in a single biological sample. For instance it can be possible to measure the two forms of Hcrt-1 in a single sample of CSF or plasma. (This has been termed sequential multiple antigen radioimmunoassay technique, or "SMART").

Prior to RIA, Hcrt-1 is extracted from the CSF or plasma sample. This is achieved by acidification of the sample with 1% TFA followed by loading onto a C18 Sep-Column, washing the column with 1% TFA, and eluting the peptide with 1% TFA/40% acetonitrile. The eluant is then dried down and re-suspended in RIA buffer ready for assay.

Preparation of the Plates and Assay Protocol

The 96-well plates are first coated with protein A (Sigma, binding capacity 9-11 mg of human IgG per mg) by adding 0.1 µg in 100 µl of 0.1M sodium bicarbonate, pH9, to each well. The plates are normally prepared in advance and can be stored for several weeks at 4° C. when tightly wrapped to prevent drying out. However; it is possible to use them after approximately 2 h incubation at room temperature. The protein A solution is then discarded and the plates washed 3 times in a wash buffer consisting of 0.15M K2HPO4, 0.2 mM ascorbic acid, 0.2% Tween 20, pH7.5 and blotted on a paper towel. Next, 200 µl of assay buffer (same as wash buffer plus 0.1% gelatin) is pipetted into each well and left at room temperature for 30 min. This step is included in an attempt to remove protein A bound with only low affinity to the plate which might otherwise dissociate at later stages in the assay thereby removing bound antibody and tracer. After dumping this solution and blotting, 50 µl of the appropriate concentration of antibody diluted with assay buffer is added to all but 4 wells. To these 4 wells are added assay buffer alone to provide an index of non-specific binding. The antibody dilution used is that which is pre-determined to produce 20-30% maximum binding in the assay. The wells are then left for 2 h at room temperature.

Standard solutions of Hcrt-1 are prepared in quadruplet ranging from 0.1 to 50 fmol in 50 µl. These standards (plus four blanks) are made up in RIA buffer. All dilutions are carried out in polypropylene tubes to minimize loss due to 'sticking'. The contents of each tube are then transferred to the assay wells following dumping of the antibody solution, washing 3 times with wash buffer and blotting.

A 2 h pre-incubation period at room temperature then follows. At the end of this time 50 µl of assay buffer containing approximately 5,000 CPM of $^{125}$I-labeled tracer peptide is added to each well and the plate left to incubate overnight at 4° C. (this final incubation step can be reduced to approx. 2 h with only slight loss of sensitivity). Subsequently the contents of the wells are discarded and the wells washed 3 times with wash buffer and blotted prior to addition of Microscint 20 and counting in the Top Count plate reader. Results from the Solid-Phase Radioimmunoassay (RIA) for Hypocretin (Hcrt-1) are shown below in Table I:

TABLE I

| Animal | Substance | Number of samples | Mean level fmol/ml | Range in levels fmol/ml |
|---|---|---|---|---|
| Narcoleptic dog | Cerebrospinal fluid | 22 | 53 | 26-140 |
| Narcoleptic dog | Blood serum | 12 | 11 | 5-16 |
| Normal human | Cerebrospinal fluid | 35 | 62 | 21-203 |
| Normal human | Blood serum | 3 | 10 | 8-14 |

The present invention is not to be limited in scope by the exemplified embodiments which are intended as illustrations of single aspects of the invention. Indeed, various modifications of the invention in addition to those described herein will become apparent to those skilled in the art from the foregoing description and accompanying drawings. Such modifications are intended to fall within the scope of the appended claims.

All publications and patent documents cited above are hereby incorporated by reference in their entirety for all purposes to the same extent as if each were so individually denoted.

CROSS-REFERENCES TO RELATED APPLICATIONS

Not Applicable

What is claimed is:

1. A method of increasing gross motor activity in an individual comprising administering an effective dosage regime of hypocretin-1 or hypocretin-2 to a peripheral tissue in the individual sufficient to increase gross motor activity in the individual as measurable by an activity monitor;
wherein the individual is overweight, suffers from a weight disorder, or suffers from obesity.

2. The method of claim 1, wherein the individual has excess body weight before the administering step and the administering reduces the excess body weight.

3. The method of claim 1, further comprising monitoring a sign of the excess body weight responsive to the administering.

4. The method of claim 3, wherein the sign of the excess body weight is a body mass index, waist circumference, waist to hip ratio, skin fold thickness, body density, body weight, or body fat percentage of the individual.

5. The method of claim 1, wherein the administering is by intraparenchymal injection, intravenous infusion, intraperitoneal injection, transdermal delivery, intramuscular delivery, subcutaneous delivery, inhalation, nasal, rectal, or oral delivery.

6. The method of claim 1, wherein the individual suffers from a weight disorder.

7. The method of claim 6, wherein the weight disorder is due to a deficiency of a hypocretin, a hypocretin agonist, or a hypocretin receptor in the individual.

8. The method of claim 6, wherein the weight disorder is due to a deficiency in a hypocretin receptor transduction pathway in the individual.

9. The method of claim 1, wherein the individual suffers from obesity.

10. The method of claim 9, wherein obesity is determined based on a sign of excess body weight selected from the group consisting of body mass index, waist circumference, waist to hip ratio, skin fold thickness, body density, body weight, and body fat percentage.

11. The method of claim 9, wherein the individual has a body mass index of 30 or higher before beginning the administering step.

12. The method of claim 1, wherein the individual is overweight.

13. The method of claim 1, wherein the administering causes an increase in the individual's caloric output relative to the individual's caloric intake.

14. The method of claim 1, wherein the hypocretin is administered with a pharmaceutically acceptable carrier as a pharmaceutical composition.

15. The method of claim 1, wherein the individual is free of narcolepsy.

16. A method of increasing locomotion in an individual, the method comprising administering an effective dosage regime of hypocretin-1 or hypocretin-2 to a peripheral tissue in the individual;
wherein the individual is overweight, suffers from a weight disorder, or suffers from obesity.

17. The method of claim 16, further comprising monitoring the locomotion in the individual responsive to the administering.

18. A method of treating an individual who is overweight, suffers from a weight disorder, or suffers from obesity comprising administering an effective dosage regime of hypocretin-1 or hypocretin-2 to a peripheral tissue in the individual sufficient to increase gross motor activity in the individual as measurable by an activity monitor,
wherein the individual shows a behavioral symptom of a weight disorder, and wherein the behavioral symptom is selected from the group consisting of inactivity, overeating, and high calorie food selection.

* * * * *

UNITED STATES PATENT AND TRADEMARK OFFICE
CERTIFICATE OF CORRECTION

| | | |
|---|---|---|
| PATENT NO. | : 7,662,780 B2 | Page 1 of 1 |
| APPLICATION NO. | : 10/526110 | |
| DATED | : February 16, 2010 | |
| INVENTOR(S) | : Jerome Siegel and Lisa Noelle Boehmer Murillo | |

It is certified that error appears in the above-identified patent and that said Letters Patent is hereby corrected as shown below:

Please insert the following text above the TECHNICAL FIELD section, Col. 1, Line 5:

-- This invention was made with Government support under Grant No. NS014610 awarded by the National Institutes of Health. The Government has certain rights in this invention. --

Signed and Sealed this
Twelfth Day of March, 2013

Teresa Stanek Rea
*Acting Director of the United States Patent and Trademark Office*